(12) United States Patent
Karakozian

(10) Patent No.: US 6,451,016 B1
(45) Date of Patent: Sep. 17, 2002

(54) DISPLACEABLE ABLATION ELECTRODE

(75) Inventor: Sarkis Karakozian, Belmont, MA (US)

(73) Assignee: C. R. Bard, Inc., Billerica, MA (US)

( * ) Notice: Subject to any disclaimer, the term of this patent is extended or adjusted under 35 U.S.C. 154(b) by 0 days.

(21) Appl. No.: 09/351,517

(22) Filed: Jul. 12, 1999

(51) Int. Cl.$^7$ .............................................. A61B 18/18
(52) U.S. Cl. ...................................... 606/41; 600/374
(58) Field of Search ............................ 606/41, 46, 47, 606/48, 49, 50; 600/374, 381; 604/95.04

(56) References Cited

U.S. PATENT DOCUMENTS

| | | |
|---|---|---|
| 452,220 A | 5/1891 | Gunning |
| 1,963,636 A | 6/1934 | Wappler |
| 2,102,270 A | 12/1937 | Hyams |
| 2,888,017 A | 5/1959 | Wallace |
| 4,565,200 A | 1/1986 | Cosman ..................... 128/642 |
| 4,664,120 A | 5/1987 | Hess .......................... 128/642 |
| 5,035,695 A | 7/1991 | Weber, Jr. et al. ............ 606/42 |
| 5,163,938 A | 11/1992 | Kambara et al. ............. 606/47 |
| 5,197,964 A | 3/1993 | Parins ........................ 606/48 |
| 5,290,286 A | 3/1994 | Parins ........................ 606/50 |
| 5,327,889 A | 7/1994 | Imran ......................... 128/642 |
| 5,431,696 A | 7/1995 | Atlee, III .................... 607/124 |
| 5,482,037 A | 1/1996 | Borghi ....................... 128/642 |
| 5,487,385 A | 1/1996 | Avitall ....................... 128/642 |
| 5,651,785 A | 7/1997 | Abela et al. ................. 606/15 |
| 5,681,280 A * | 10/1997 | Rusk et al. .................. 604/95 |
| 5,752,915 A | 5/1998 | Neubauer et al. ........... 606/373 |
| 5,788,692 A | 8/1998 | Campbell et al. ............ 606/33 |
| 5,803,083 A | 9/1998 | Buck et al. ............ 128/660.03 |
| 5,824,030 A | 10/1998 | Yang et al. .................. 607/122 |
| 5,885,278 A | 3/1999 | Fleischman .................. 606/41 |
| 5,904,711 A * | 5/1999 | Flom et al. .................. 607/129 |
| 5,910,129 A * | 6/1999 | Koblish et al. ............... 604/95 |
| 5,997,536 A | 12/1999 | Osswald et al. .............. 606/47 |

FOREIGN PATENT DOCUMENTS

| | | | |
|---|---|---|---|
| EP | 0 609 182 A1 | 12/1994 | |
| EP | 0 842 640 A1 | 5/1998 | ........... A61B/17/39 |
| WO | 97/42893 | 11/1997 | ........... A61B/17/39 |

* cited by examiner

*Primary Examiner*—Rosiland S. Kearney
(74) *Attorney, Agent, or Firm*—Darby & Darby

(57) ABSTRACT

An ablation catheter comprising, in an exemplary embodiment, a probe having a proximal end and a distal end and an electrode which is axially displaceable along the probe. A first pull cable is attached to the electrode, extends from the electrode towards the distal end of the probe, and doubles back through the catheter for pulling the electrode toward the distal end of the probe. The first pull cable is disposed within a lumen formed in the catheter that extends substantially from the distal end to the proximal end. A second pull cable is attached to the opposite end of the electrode and extends from the electrode toward the proximal end of the catheter for pulling the electrode away from the distal end. The second pull cable is disposed within a lumen formed in the catheter. Both pull cables are coupled to an actuator mechanism at the proximal end of the catheter for effecting axial movement of the electrode relative to the distal tip of the probe by selectively tensioning the respective pull cables.

17 Claims, 5 Drawing Sheets

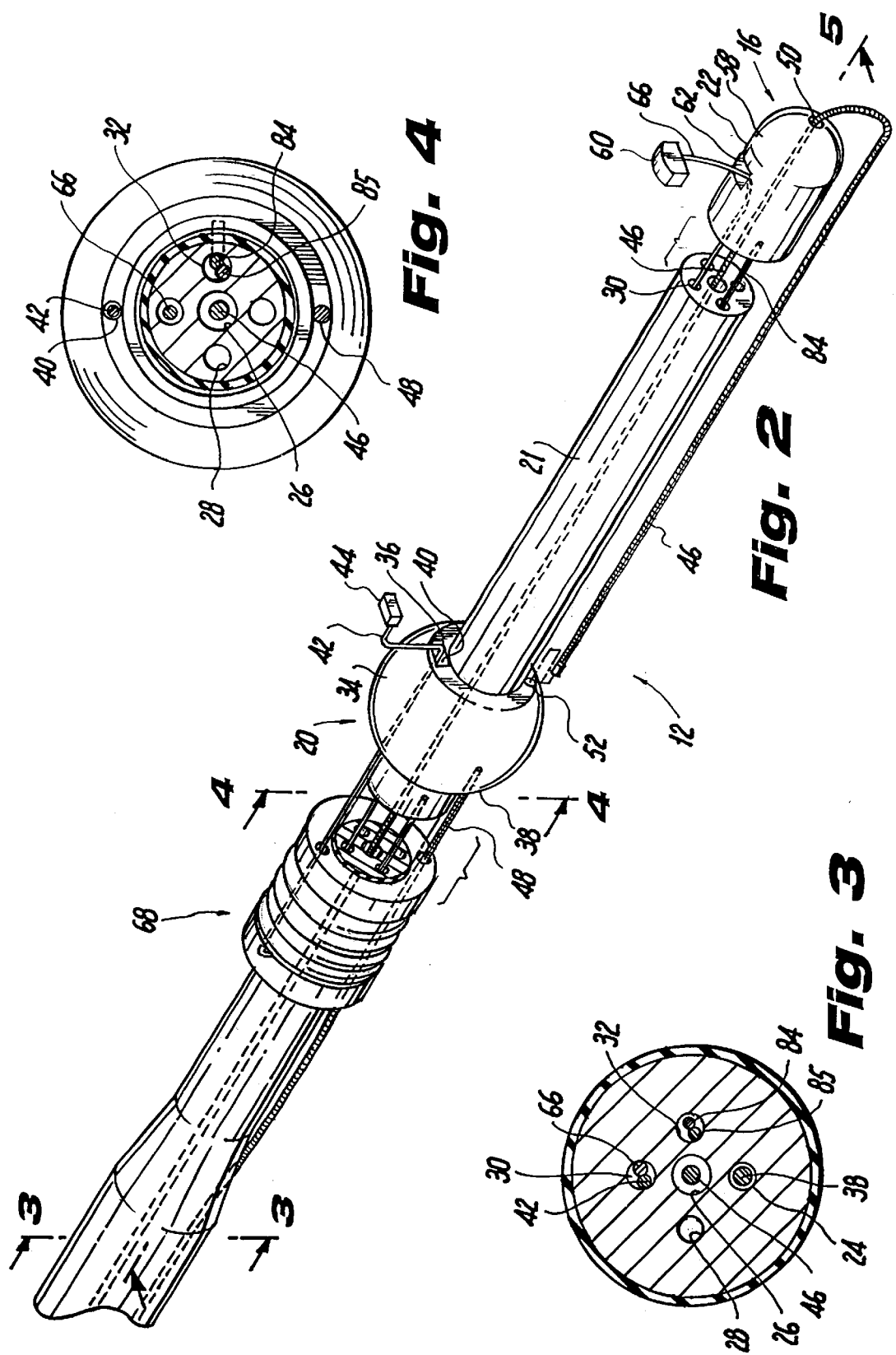

DISPLACEABLE ABLATION ELECTRODE

BACKGROUND

1. Field of the Invention

The present invention relates generally to catheters, and more particularly, to an ablation catheter for use in heart surgery, the catheter having an axially displaceable electrode to allow the formation of long endocardial lesions in the cardiac chambers of the heart.

2. Description of the Prior Art

A representative prior art ablation catheter having a movable electrode is disclosed in PCT/GB97/01270 to Morgan et al., the rights to which are assigned to the assignee of the present invention. The Morgan application discloses a catheter having a sliding ring electrode telescopically disposed over the catheter shaft and a remote mounted actuator for moving the sliding electrode. A sheathed conductor is disposed in a longitudinal channel formed in the catheter. The conductor is connected at one end to a controllable source of RF energy and at a second end to the conductor. The sheath provides electrical insulation for the conductor as the conductor is moved axially along the probe shaft. The actuator mechanism is configured to push or pull the electrode towards and away from the distal end of the probe by advancing or withdrawing the sheathed conductor along the catheter shaft. In this manner, contiguous endocardial lesions may be created in the cardiac chambers by applying radio frequency current to the sliding electrode. This expedient requires, however, that the conductor/actuator wire have sufficient column strength to resist buckling under load.

SUMMARY OF THE INVENTION

It is an object of the present invention to provide an ablation catheter having a sliding electrode for creating endocardial lesions.

It is a further object of the invention to provide an ablation catheter having a sliding electrode in which "pull" wires or cables are employed for improved actuation with better reliability.

It is yet another object of the invention to provide an ablation catheter having a sliding electrode which reduces the likelihood of actuation wire kinking or damage.

It is yet another object of the invention to provide an ablation catheter having a movable electrode which can be displaced in successive, predetermined increments to create continuous endocardial lesions.

In accordance with the above objects and additional objects that will become apparent hereinafter, the present invention provides an ablation catheter comprising, in an exemplary embodiment, a probe having a proximal end and a distal end and an electrode which is axially displaceable along the probe. A first pull cable is attached to the electrode, extends from the electrode towards the distal end of the probe, and doubles back through the catheter for pulling the electrode toward the distal end of the probe. The first pull cable is disposed within a lumen formed in the catheter that extends substantially from the distal end to the proximal end. A second pull cable is attached to the opposite end of the electrode and extends from the electrode toward the proximal end of the catheter for pulling the electrode away from the distal end. The second pull cable is disposed within a lumen formed in the catheter. Both pull cables are coupled to an actuator mechanism at the proximal end of the catheter for effecting axial movement of the electrode relative to the distal tip of the probe by selectively tensioning the respective pull cables. A second electrode may be provided at the distal end of the catheter. In that arrangement, the first pull cable exits the catheter through an opening in the fixed electrode.

BRIEF DESCRIPTION OF THE DRAWINGS

In accordance with the above, the present invention will now be described in detail with particular reference to the accompanying drawings.

FIG. 2 is an exploded isometric view of the probe tip;

FIG. 3 is a sectional view taken along lines 3—3 in FIG. 2;

FIG. 4 is a sectional view taken along lines 4—4 in FIG. 2;

DETAILED DESCRIPTION OF THE PREFERRED EMBODIMENTS

Figure 1:
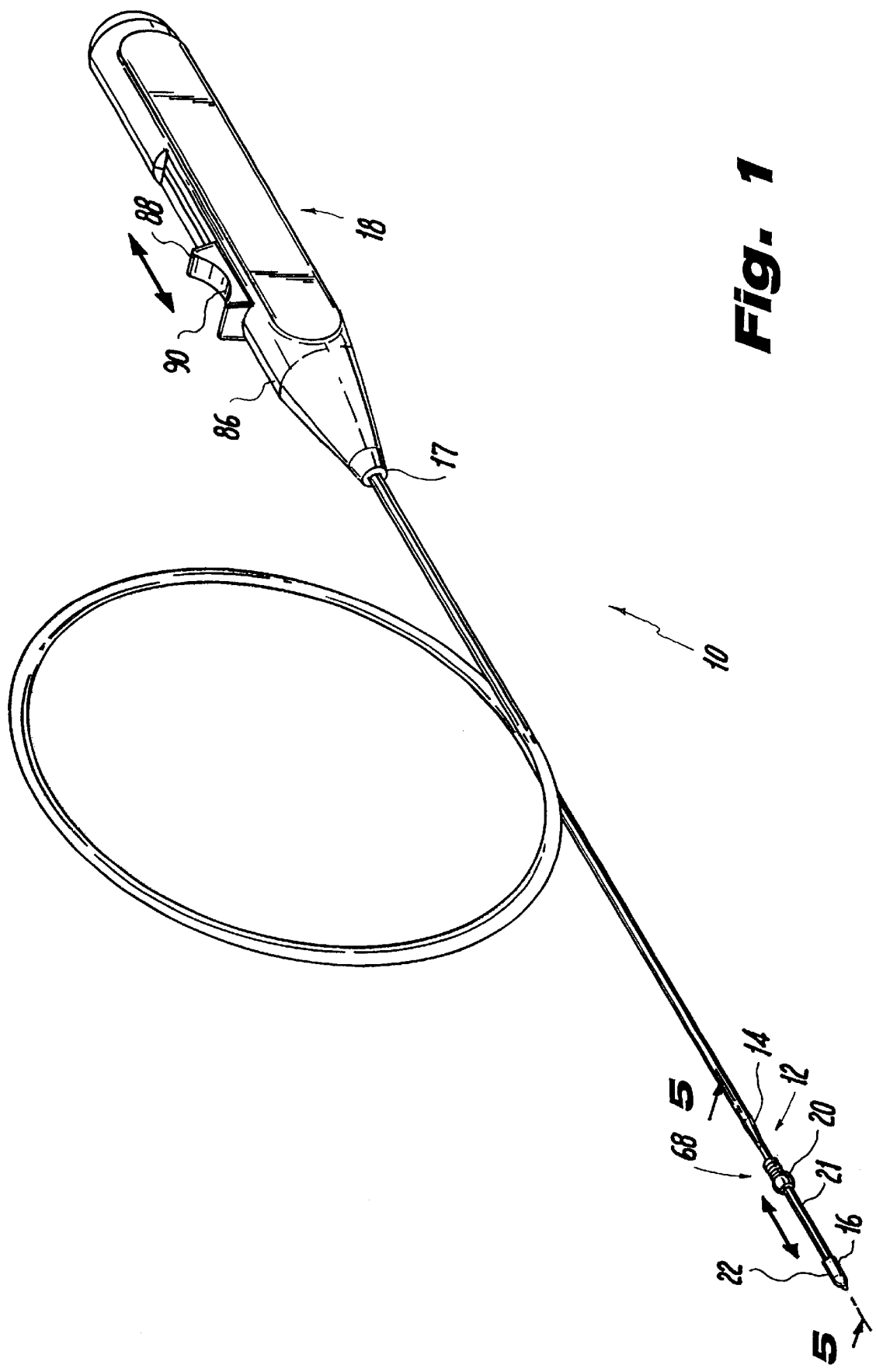
FIG. 1 is an isometric view of the ablation catheter assembly in accordance with the present invention.

Referring to the several views of the drawings, there is shown an ablation catheter generally characterized by the reference numeral 10.

As shown in FIGS. 1–5, the ablation catheter 10 generally comprises a probe 12 having a proximal end 14 and a distal end 16. An actuator 18 is coupled to a proximal end 17 of the catheter to effect axial displacement of an electrode 20 which is axially displaceable along the outer surface 21 of the probe 12. A fixed electrode 22 is disposed at the distal end 16 of the catheter 10. In the illustrative embodiment, the catheter 10 is of conventional construction with 6F or 7F tip stock (although other sizes may be used). The catheter body defines a plurality of lumens 24, 26, 28, 30 and 32 there through, the purposes of which are described in more detail below. The catheter probe extends from a tapered transition region defined in the catheter body.

Figure 5:
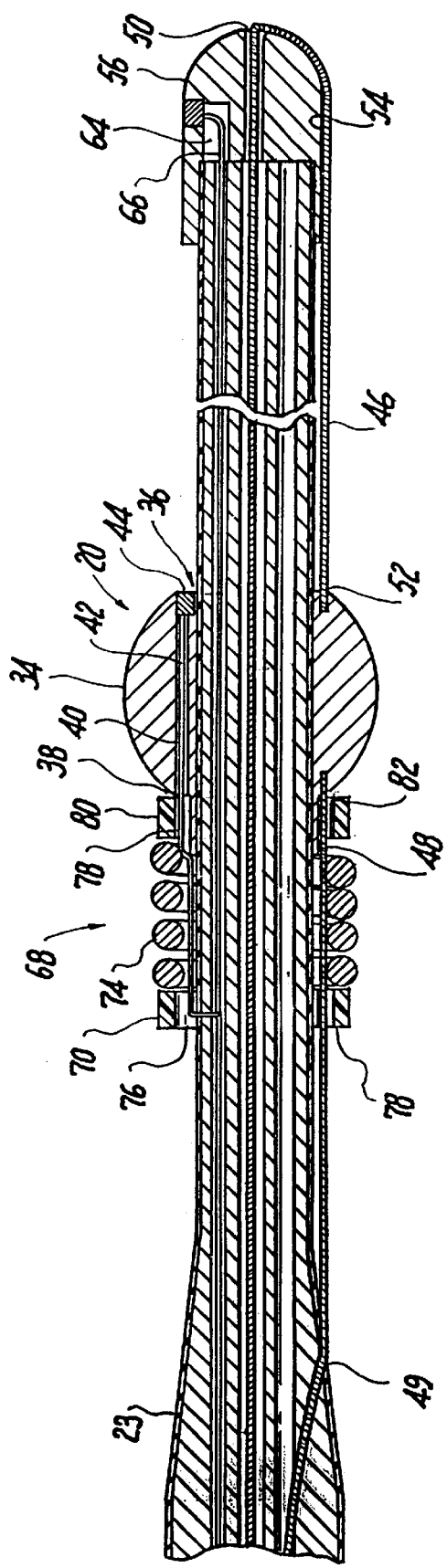
FIG. 5 is a sectional view taken along lines 5—5 in FIGS. 1 and 2.

The movable electrode 20 is axially displaceable towards and away from the distal electrode 22 at the distal tip 16 of the probe 12. The electrode 20 is preferably constructed as shown with a convex outer contact surface 34 (which may otherwise be flat or shaped as desired) bounded by a first planar face 36 and a second planar face 38. The electrode 20 is made from a metallic material, preferably with a high platinum content as is well known. Referring now to FIG. 5, the electrode 20 defines a cutout 40 there through for receiving a wire 42 to communicate electrical signals to a thermistor 44. The thermistor 44 is potted or mounted in a cavity defined in the face 36 of the electrode. Alternatively, the thermistor 44 may be located in the opposite planar face 38 disposed towards the proximal end 14 of the probe. Axial displacement of the electrode 20 is facilitated through the use of dual "pull wires" 46 and 48. This arrangement overcomes the disadvantages with prior art "push" devices in which the actuating cable must have sufficient column strength to avoid buckling under load.

The first pull wire 46 is disposed in the central lumen 26 of the catheter body for its entire length. The first pull wire 46 exits the distal tip 16 from a central bore 50 defined in the tip electrode 22, and is folded back along the catheter exterior to join the electrode 20 at an interface 52 on the planar face 36. As depicted in FIG. 5, the first pull cable 46 resides in a channel, slot or groove 54 formed in the exterior surface 56 of the tip electrode 22. Displacement of electrode 20 towards the distal tip 16 is effected by drawing the first pull wire rearwardly towards the proximal end of the catheter 10 as described in more detail below. The electrode 20 is moved in the opposite direction by the second pull wire 48, which is coupled to an interface 58 on the face 38 of the electrode 20. The respective pull wires may be soldered into the electrode 20 or attached by equivalent or different methods. Pull wire 48 extends through aperture 49 and lumen 24 of the catheter body to the actuator mechanism described in more detail below. The tip electrode 22, like the movable electrode 20, may be provided with a separate thermistor 60 for sensing temperature at the distal tip 16. The thermistor 60 is potted or mounted in a cavity or cut out 62 which opens to a space 64 to provide a conduit for an electrical wire 66 which passes through lumen 30 in the catheter body. The installation of thermistor hardware in a catheter and electrode assembly is well known to persons of skill in the art and need not be described in detail.

A retaining ring assembly 68 is provided to confine pull wire actuation in the rearward direction towards the proximal end 14 of the probe. The retaining ring assembly 68, in one embodiment, comprises a first ring 70, a second ring 72, and an intermediate compression spring 74. The spring 74 is an option and the entire assembly 68 may be replaced by a single retaining ring. In the depicted embodiment, the rings 70, 72 are provided with respective cutouts 76, 78 and 80, 82 for passing the thermistor wire 42 and the pull cable 48 to the movable electrode 20 as depicted in FIG. 5. It can also be seen that the thermistor wire 42 transitions from the retaining ring 70 through the catheter wall and into the lumen 30 where it resides alongside the other thermistor wire 66 that communicates with the distal tip electrode 22.

Each electrode is provided with a connection to an RF energy source (not shown) of the type well known in the art. In one embodiment, either pull cable 46 or 48 may be fabricated from an electrically conductive material to communicate with the RF energy source. The pull cable operates as a conductor and is accordingly provided with an outer layer of insulation, in effect a "sheathed conductor." Similarly, the outer surface 21 of the probe contains electrically insulating material to electrically isolate the respective conductors 20, 22 from each other. This may be coated with a hydrophobic material. Alternatively, a separate insulated conductor as shown in FIGS. 3 and 4 may be provided. However, if a separate conductor is employed, it must be able to translate axially as the electrode 20 moves along the probe. The tip electrode 22 communicates with the RF source via an insulated electrical wire 84 disposed in lumen 32 (see FIGS. 2 and 3). The probe components (excluding the electrodes) may be coated with chemicals having anticoagulation properties, such as, for example, Heparin or Ticlopedine, or related compounds. Although the illustrative embodiment is shown and described with a pair of electrodes, a single movable electrode may be provided and the tip electrode omitted if desired.

Using known technology in the field of ablation catheters, the portion of the probe shaft over which the electrode 20 is displaced, may be flexed, extended or rotated by axial or rotational displacement of a collar associated with the actuator mechanism. Alternatively, a replaceable stylet may be fitted over the distal end 16 of the probe to permit a range of stylets having different end curvatures to be introduced into and advanced over the distal tip 16.

Figure 6:
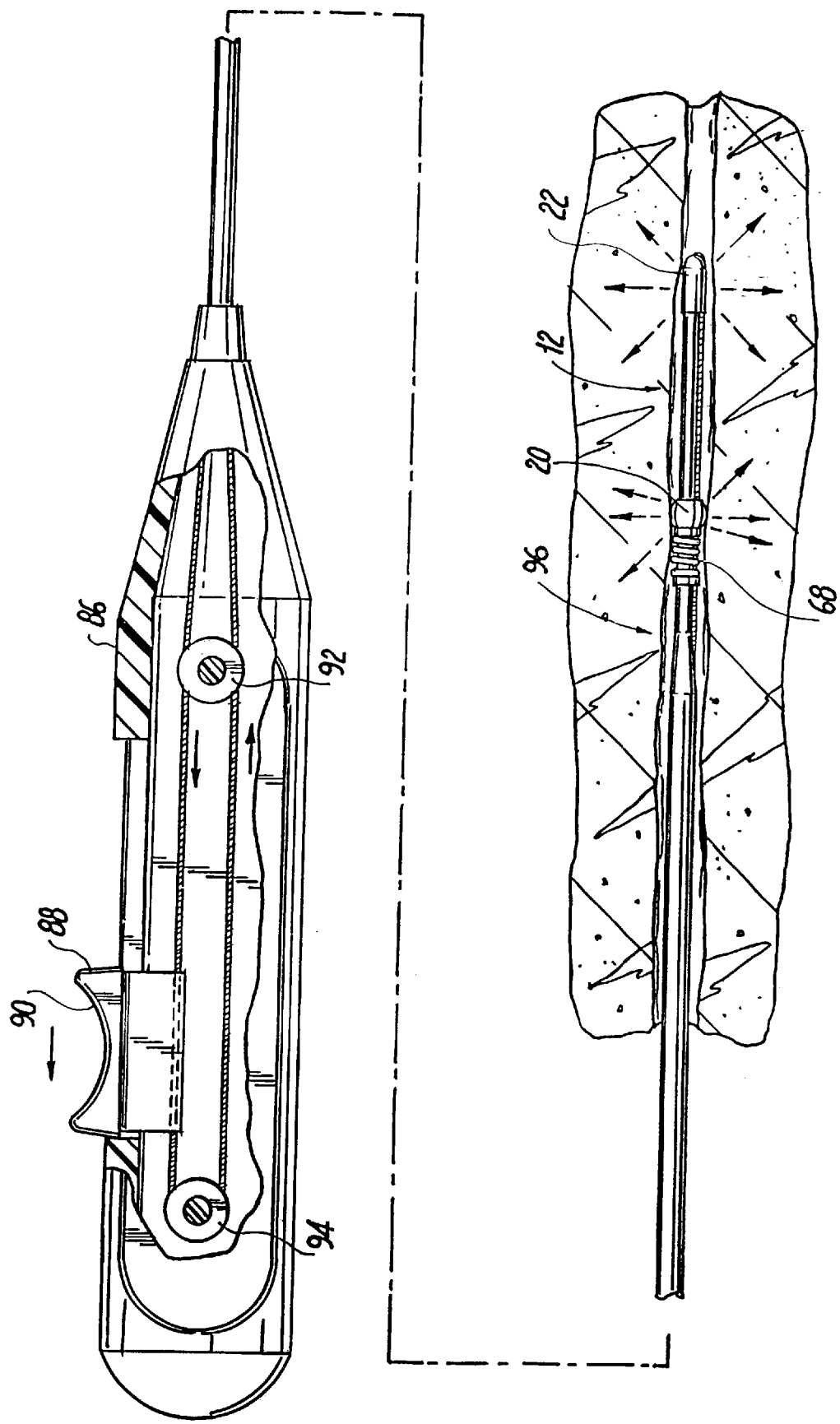
FIG. 6 is a partial sectional view of the catheter probe in a body lumen or chamber and a detail view of an exemplary actuator interior when the actuator is advancing the sliding electrode towards the distal tip.
Figure 7:
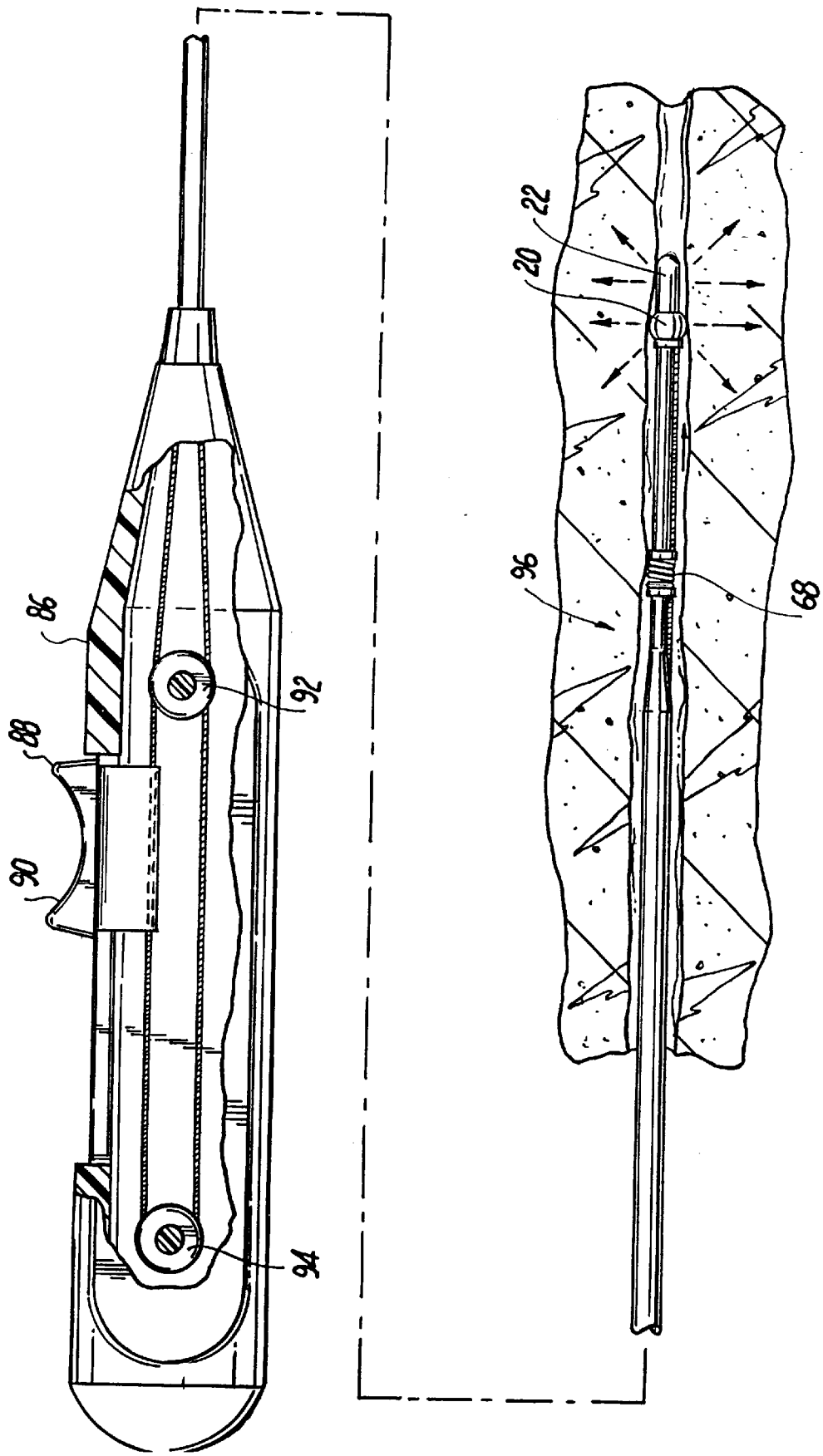
FIG. 7 is a partial sectional view of the catheter probe in a body lumen or chamber and a detail view of an exemplary actuator interior when the actuator is retracting the sliding electrode away from the distal tip.

Referring now to FIGS. 6 and 7, an illustrative embodiment of the actuator 18 includes an actuator handle (or housing) 86 having an axially displaceable element 88 which is provided with a curved surface 90 for engaging the thumb of the user. As shown schematically, the movable element 88 is coupled to the pull wires 46 and 48 via a pair of pulleys 92 and 94 to effect consequent movement of electrode 20. When the element 88 is translated in the "forward" direction towards the tapered end of the handle 86 (FIG. 6), the pull cable 46 is placed in tension so as to advance the electrode 20 towards the distal tip 16 within the affected area of the body 96 undergoing ablation. Conversely, when the element 88 is drawn in the "reverse" direction (FIG. 7), the pull cable 48 is placed in tension thereby causing the electrode 20 to move rearwardly towards the retaining ring assembly 68. In this manner, the electrode 20 can be displaced in successive, predetermined increments and the RF source energized to create a continuous endocardial lesion.

The depicted actuator is intended to be merely exemplary as a variety of different designs may be employed within the scope of the invention. For example, the aforementioned prior art Morgan application discloses an actuator assembly in FIG. 2 (the following description is with reference to the Figs. and reference numerals in the Morgan application) which comprises a ratchet mechanism 27 including a worm screw drive assembly composed of a worm screw 40 and a worm wheel 41. Manual rotation of the wheel 41 causes axial movement of the worm screw 40 and corresponding axial displacement of the movable conductor 10 coupled to the movable electrode 3.

This arrangement may be adapted to the present invention by coupling the respective first and second pull cables 46 and 48 to the respective ends of the worm screw via a pulley arrangement as described above.

The present invention has been shown in what are considered to be the most preferred and practical embodiments. It is anticipated, however, that departures may be made therefrom and that obvious modifications will be implemented by those skilled in the art.

What is claimed is:

1. An ablation catheter, comprising:
   said catheter having a proximal end and a distal end;
   a probe having a proximal end and a distal end and a linear axis;
   an electrode which is axially displaceable along said axis of said probe, said electrode having a proximal end and a distal end;
   first means attached to said distal end of said electrode for pulling said electrode along the axis of said probe toward said distal end of said probe; and
   second means attached to said proximal end of said electrode for pulling said electrode along the axis of said probe toward said proximal end of said probe.

2. The ablation catheter recited in claim 1, further comprising a second electrode disposed at said distal end of said probe.

3. The ablation catheter recited in claim 1, wherein said first means for pulling comprises a first pull cable extending toward said distal end of said catheter from said distal end of said electrode.

4. The ablation catheter recited in claim 3, wherein said second means for pulling comprises a second pull cable extending from said proximal end of said electrode toward said proximal end.

5. The ablation catheter recited in claim 4, wherein said second pull cable is disposed within a lumen formed in said catheter.

6. The ablation catheter recited in claim 3, wherein said first pull cable is disposed within a lumen formed in said catheter from said distal end of said catheter to said proximal end of said catheter.

7. The ablation catheter recited in claim 3, wherein said electrode defines a slot therein and said first pull cable is disposed within said slot.

8. The ablation catheter recited in claim 1, further comprising a retainer associated with said catheter that defines a stop travel limit for said electrode.

9. The ablation catheter recited in claim 8, wherein said probe includes a shaft and said electrode is displaceable about said shaft between said first electrode and said retainer.

10. The ablation catheter recited in claim 8, wherein said retainer includes a compression spring for biasing said movable electrode against movement away from said distal end of said probe.

11. The ablation catheter recited in claim 10, wherein said retainer further comprises a pair of retaining rings bounding said spring, said retaining rings being anchored to said probe.

12. The ablation catheter recited in claim 1, further comprising an actuator for displacing said electrode towards and away from said distal end of said catheter.

13. An ablation catheter, comprising:

said catheter having a proximal end and a distal end;

a probe having a proximal end and a distal end and a linear axis;

a first electrode associated with said distal end of said catheter;

a second electrode which is axially displaceable along said axis of said probe, said second electrode having a proximal end and a distal end;

a first pull cable extending toward said distal end of said catheter from said second electrode and attached to said distal end of said second electrode for pulling said second electrode along the axis of said probe toward said distal end of said probe, said first pull cable being disposed within a lumen formed in said catheter from said distal end to said proximal end of said catheter; and a second pull cable extending from said second electrode toward said proximal end of said catheter and attached to said proximal end of said second electrode for pulling said second electrode along the axis of said probe away from said distal end of said catheter, said second pull cable being disposed within a lumen formed in said catheter.

14. The ablation catheter recited in claim 13, further comprising a retainer associated with said catheter that defines a stop travel limit for said second electrode.

15. The ablation catheter recited in claim 13, wherein said probe includes a shaft and said second electrode is displaceable along said shaft between said first electrode and said retainer.

16. The ablation catheter recited in claim 13, wherein said first electrode defines a slot therein and said second pull cable is disposed within said slot.

17. The ablation catheter recited in claim 13, further comprising an actuator for displacing said second electrode towards and away from said distal end of said catheter.

* * * * *